(12) United States Patent
Ramhold et al.

(10) Patent No.: US 9,346,830 B2
(45) Date of Patent: May 24, 2016

(54) METHOD FOR PRODUCING AMINO ACID CHELATE COMPOUNDS, AMINO ACID CHELATE COMPOUNDS AND USE OF AMINO ACID CHELATE COMPOUNDS

(75) Inventors: Dietmar Ramhold, Pronstorf (DE); Eberhard Gock, Goslar (DE); Edmund Mathies, Moorrege (DE); Wolfram Strauch, Hamburg (DE)

(73) Assignee: ISF AG, Pinneberg (DE)

( * ) Notice: Subject to any disclaimer, the term of this patent is extended or adjusted under 35 U.S.C. 154(b) by 146 days.

(21) Appl. No.: 14/000,101

(22) PCT Filed: Nov. 24, 2011

(86) PCT No.: PCT/EP2011/004237
§ 371 (c)(1),
(2), (4) Date: Oct. 16, 2013

(87) PCT Pub. No.: WO2012/110063
PCT Pub. Date: Aug. 23, 2012

(65) Prior Publication Data
US 2014/0037960 A1 Feb. 6, 2014

(30) Foreign Application Priority Data
Feb. 17, 2011 (DE) .......................... 10 2011 011 924

(51) Int. Cl.
| | |
|---|---|
| *C07F 1/08* | (2006.01) |
| *C07C 227/16* | (2006.01) |
| *C07C 229/76* | (2006.01) |
| *C07F 3/06* | (2006.01) |
| *C07F 13/00* | (2006.01) |
| *C07F 15/02* | (2006.01) |
| *C07F 15/04* | (2006.01) |

(52) U.S. Cl.
CPC ................. *C07F 1/08* (2013.01); *C07C 227/16* (2013.01); *C07C 229/76* (2013.01); *C07F 3/06* (2013.01); *C07F 13/005* (2013.01); *C07F 15/025* (2013.01); *C07F 15/045* (2013.01); *Y10T 428/2982* (2015.01)

(58) Field of Classification Search
CPC ............ C07F 1/08; C07F 3/06; C07F 15/025; C07F 15/045; C07F 13/005; C07C 227/16; C07C 229/76
USPC ............................................ 428/402; 556/40
See application file for complete search history.

(56) References Cited

U.S. PATENT DOCUMENTS

| | | | | |
|---|---|---|---|---|
| 830,716 | A | | 9/1906 | Hermanson |
| 4,315,927 | A | * | 2/1982 | Evans ........................... 514/188 |
| 4,599,152 | A | * | 7/1986 | Ashmead ....................... 205/435 |
| 4,814,177 | A | * | 3/1989 | Walsdorf et al. .............. 424/464 |
| 5,516,925 | A | * | 5/1996 | Pedersen et al. ................ 556/50 |

FOREIGN PATENT DOCUMENTS

| | | | |
|---|---|---|---|
| DE | 102004036486 | * | 3/2005 |
| DE | 10 2004 039 486 A1 | | 2/2006 |
| EP | 1 529 775 A1 | | 5/2005 |
| EP | 1529775 | * | 5/2005 |
| RU | 2104995 C1 | | 2/1998 |

OTHER PUBLICATIONS

Komorita et al., "Metal complexes with Amino Acid Amides . . . " Bulletin of the Chemical Society of Japan, vol. 42 168-177 , 1969.*
Matsuoka et al., "Studies of the mixed Amino-acid Compexes . . . " Bulletin of the Chemical Society of Japan, vol. 39, 1257-1261, 1966.*
Herlinger et al., "Infrared spectra of Amino Acids and their Metal Complexes . . . " JOACS 92:22, Nov. 4, 1970.*
Denning, Optical Activity, Absolute Configuration, and Rearrangement Reactions of Tris Amino Acis Complexes of Cobalt (III) with L-Alanine, L-Leucine, and L-Proline, Inorganic Chemistry, University of Illinois, Urbana, Illinois, pp. 1056-1065, vol. 5 No. 6, Jun. 1966.
Herlinger, et al., Infrared Spectra of Amino Acids and Their Metal Complexes/ II. Geometrical Isomerism in Bis (amino acidato) copper (II) Complexes, Journal of the American Chemical Society, pp. 6474-6481, 92:22, Nov. 4, 1970.
Matsuoka, et al., Studies of the Mixed Amino-acid Complexes of Complexes of Cobalt (III). I. The Geometrical Isomers of the [Co en gly (chelate)] Series, Bulletin of the Chemical Society of Japan, pp. 1257-1261, vol. 39, Jun. 1966.
Komorita, et al., Metal Complezes with Amino Acid Amides. II. Preparations and Circular Dichrosim Behavior of Copper (II) Complexes, Bulletin of the Checmical Society of Japan, pp. 168-177, vol. 42, Jan. 1969.

* cited by examiner

*Primary Examiner* — Leszek Kiliman
(74) *Attorney, Agent, or Firm* — Vidas, Arrett & Steinkraus

(57) ABSTRACT

A method for producing amino acid chelate compounds, characterized in that metal oxides and/or metal carbonates and/or metal sulfates and/or metal chlorides and/or metal hydroxides in solid form are activated mechanically and then the activated metal oxides and/or metal carbonates and/or metal hydroxides and/or metal sulfates and/or metal chlorides are brought together with amino acids in solid form and converted to amino acid chelate compounds in a solid-state reaction.

28 Claims, 2 Drawing Sheets

METHOD FOR PRODUCING AMINO ACID CHELATE COMPOUNDS, AMINO ACID CHELATE COMPOUNDS AND USE OF AMINO ACID CHELATE COMPOUNDS

CROSS-REFERENCE TO RELATED APPLICATIONS

This is a national stage application of PCT/EP2011/004237, filed on Nov. 24, 2011, which claims priority to DE 10 2011 011 924.8 filed on Feb. 17, 2011.

STATEMENT REGARDING FEDERALLY SPONSORED RESEARCH

Not applicable.

BACKGROUND OF THE INVENTION

The invention relates to a method for producing amino acid chelate compounds. Furthermore, it relates to amino acid chelate compounds. Finally, it relates to the use of amino acid chelate compounds.

When metal compounds with amino acids undergo a reaction, so-called chelates are created. Chelate compounds exist among other things for the metals copper, zinc, manganese, iron, calcium, magnesium, cobalt, vanadium, selenium and nickel and for the amino acids glycine, lysine and methionine.

Amino acid chelate compounds are used among other places in animal food and fertilizer for supplying trace elements. Glycine chelates have been increasingly used in animal nutrition in recent years. In many tests on animals, improved performance and improved intestinal absorption with respect to trace elements made of inorganic compounds were observed. The efficiency of trace elements in food can be improved and the excretion rate can be reduced. The risk of a physiological undersupply and performance depression is reduced. Moreover, information on potential advantages of organically bound trace elements was published, e.g. improved zootechnical and reproductive performance, higher outer and inner egg quality, higher incorporation in bodily organs or tissues.

The following glycine chelates are legally permitted in food products and are currently available on the market (the E numbers according to the EU food additive regulation are specified in parentheses):
Glycine iron chelate hydrate (E1), short: iron glycinate
Glycine copper chelate hydrate (E4), short: copper glycinate
Glycine manganese chelate hydrate (E5), short: manganese glycinate
Glycine zinc chelate hydrate (E6), short: zinc glycinate The glycinates currently available on the market differ considerably in particular with respect to the trace element content, glycine content, solubility in water, colour and structure, pH value and quantity and type of inorganic anions (sulfates and chlorides). All so-called copper glycinates that have been on the market up until now are either displaced with anions and/or diluted with fillers and/or contain a glycine content that is too low for real duplicate complexing. The enormous differences are attributed to the respectively used production methods, the raw materials used and the selected reaction ratios between trace element and glycine.

The production of glycine chelates is extremely complex. It generally starts from solutions of the corresponding trace element compounds with glycine, which are brought to react at increased temperatures. Evaporation, crystallization, drying and milling follow.

The state of the art is described for example in U.S. Pat. Nos. 4,315,927A, 4,814,177A, 830,716A, 4,599,152A and 5,516,925A.

The patent application CN 2009/10030766.3 describes the production of zinc glycinate. Then, in the first step, 5 to 15% glycine is stirred with 5-10% nano ZnO with water at 50°-80° C. for 3 to 24 hours and then held at rest for 6 to 10 hours. In the second step, it is centrifuged at 3,000 to 8,000 $min^{-1}$ and the centrifugate is dried in an oven at 80°-120° C. The third step comprises the crushing and the classification when greater than 80-120 mesh. In the application CN 2009/10030767.8, the same production method is described for calcium glycinate except for the omission of the centrifuging.

EP 1 529 775 B1 relates to a method for the production of chelates of metals with organic acids, which mainly work in an anhydrous medium. Metal oxides, hydroxides or salts are used. The organic acid ligand such as glycine, lysine, glutamic acid among other things and the respective metal compounds such as hydroxides like copper hydroxide, zinc hydroxide, iron hydroxide, manganese hydroxide etc. are immersed in anhydrous liquids like methanol, ethanol, i-propanol, hexane, petroleum ether etc. and mixed together at room temperature or at an increased temperature. Since water is also a reaction product, it must be removed with the help of a water separation device (e.g. Dean-Stark water separator). The removal of the respective metal chelate from the organic liquid takes place through filtration. After drying, the respective metal chelate represents a very fine powder as the finished product.

It can be seen in the exemplary embodiment in EP 1 529 775 B1 that the described production method requires a pretreatment of the used metal compounds. Thus, for example, the production of copper hydroxide starts with $CuSO_4.5H_2O$, which is stabilized with KOH at pH 10-11 for the precipitation of $Cu(OH)_2$. This is followed by a double centrifugation, which is accompanied by washing processes in ethanol. For the production of copper glycinate, $Cu(OH)_2$ is then mixed with glycine and this mixture is boiled in ethanol for 5 hours. The copper glycinate created under these conditions is filtered out and dried to powder.

The patent applications CN 92107282.1 and CN 2007/130121.0 describe the conversion of mixtures of copper acetate and glycine in a one-step, solid-state reaction in a ball mill. For this, a mixture of copper acetate and glycine is combined with water and sodium carbonate and subjected to wet grinding in a ball mill. After several hours of grinding, the suspension is dried, washed with ethanol, centrifuged and dried again.

DE 10 2004 039 486 A1 describes a dry process for producing organic trace element compounds. Any dry mixture of a metal oxide and a solid organic acid is exposed to mechanical stress through blows and pressure from a fine crushing machine such that the released enthalpy amount triggers a solid-state reaction into a metal salt-like compound.

The focus of this unexamined laid-open patent application is the production of zinc bismethionate made of mixtures of ZnO and methionine, which are milled together in the mixture. This is proven with a total of seven examples. The other three examples have mixtures of CuO and asparaginic acid (one of a total of 21 amino acids), mixtures of MnO and malic acid (carboxylic acid ester) as well as mixtures of $Cr(OH)_3$ and nicotinic acid (alkaloids bound in a salt-like manner to plant acids) as the object.

The testing of the method has shown that operating errors can occur through caking of ground material on the mill walls. These cakings can cause the complete cementing of the grinding chamber, which can only be remedied again with the help of air hammers and eliminates an industrial use. Moreover, the product qualities are not reproducible.

SUMMARY OF THE INVENTION

Against this background, the object of the invention is to provide a simple, stable and industrially suitable method for producing amino acid chelate compounds. Furthermore, the invention targets the creation of amino acid chelate compounds, which have advantageous production properties. Finally, advantageous uses for the amino acid chelate compounds are specified.

DETAILED DESCRIPTION OF THE INVENTION

Figure 1:
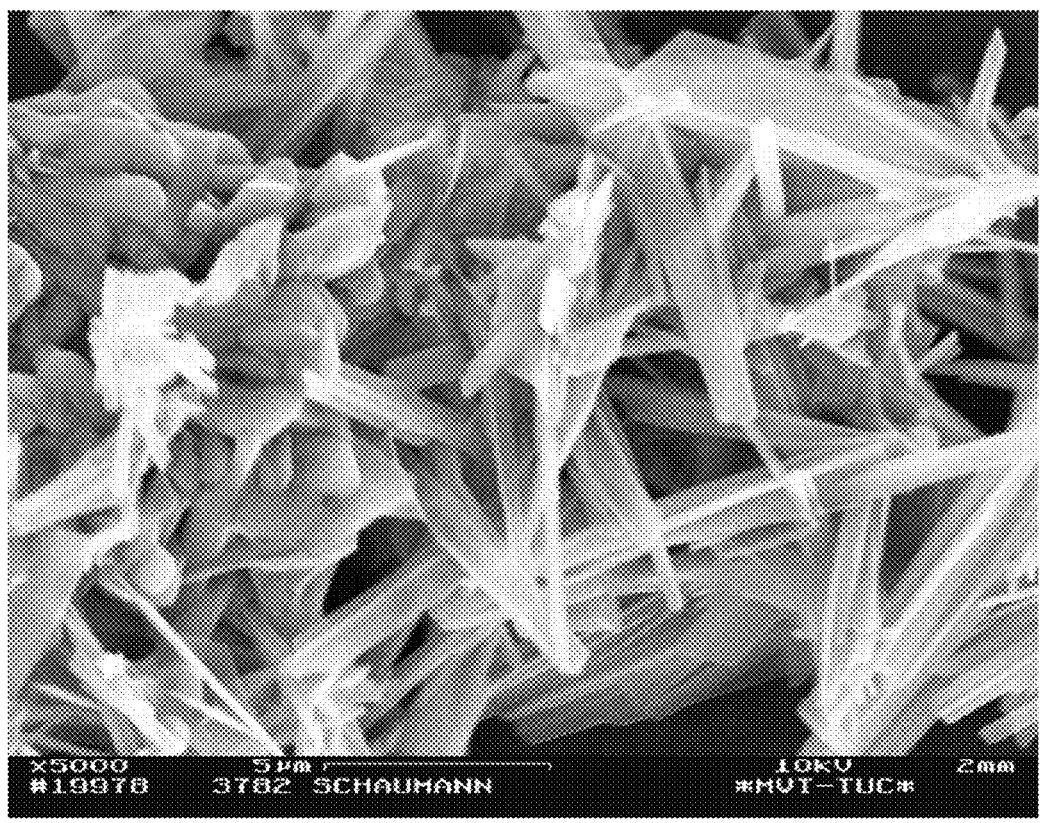
FIG. 1 shows an example of an image from the scanning electron microscope (SEM)

In the case of the method according to the invention for producing amino acid chelate compounds, metal oxides and/or metal carbonates and/or metal sulfates and/or metal chlorides and/or metal hydroxides in solid form are activated mechanically and then the activated metal oxides and/or metal carbonates and/or metal sulfates and/or metal chlorides and/or metal hydroxides are brought together with amino acids in solid form and converted to amino acid chelate compounds in a solid-state reaction.

It was found that the mechanical activation of mixtures of metal compounds and amino acids is not a suitable path. The conversion of metal compounds with the organic acid is rather a spontaneous chain-like consecutive reaction. From an energy point of view, an energy loss on a large scale thus takes place during the mechanical activation of mixtures, the greater mass fraction of which does not need a mechanical activation. This is in the order of magnitude of the mixture ratio. In the case of a mixture ratio of 1:2 (CuO to glycine), the share to be activated non-mechanically is more than 50%. The key reactant during the conversion with organic acids is the metal compound. According to the invention, this is first activated mechanically. The decoupling of the mechanical activation of the metal compound and the solid-state reaction with an amino acid leads to a decisive influence on the reaction mechanism during the synthesis of metal chelates. After the separate mechanical activation of the metal compound, the chelate solid-state reaction is triggered by the addition of amino acids. The overall conversion of the reaction is considerably improved by the separate mechanical activation of the metal compound. The metal compound and the amino acid are available in solid form in the solid-state reaction. The reaction partners are hereby dry or mainly dry, i.e. have at the most a low moisture content. Their moisture content is preferably at the most 5% by weight.

According to a preferred embodiment, the metal compounds are supplied to the mechanical activation as a mixture of loose particles. According to a further embodiment, the amino acids are supplied to the mechanically activated metal compounds in the form of a further mixture of loose particles. The mechanical activation or respectively the solid-state reaction is promoted through the use of metal compounds in the form of a mixture of loose particles or respectively amino acids in the form of a mixture of loose particles. However, it is also generally possible to supply the reaction partners to the method in the form of large connected pieces, which can be milled in execution of the method.

According to one embodiment of the method, at least one reactant is thermally activated. The thermal activation accelerates the solid-station reaction. In the case of the thermal activation, at least one reactant is heated. If the reaction temperature exceeds the boiling point of water (100° C. during execution of the reaction under normal pressure), then the free reaction water evaporates and is separated from the reactants.

According to a preferred embodiment, the thermal activation takes place simultaneously with the mechanical activation and/or with the conversion in the solid-state reaction. The thermal energy required for the thermal activation is hereby supplied in a targeted manner to the solid-state reaction. Furthermore, the thermal energy released during the mechanical activation or respectively during the execution of the solid-state reaction can be used for the thermal activation. This is in particular the case during the execution of the mechanical activation and/or the solid-state reaction in a mill or another mixed reactor.

According to a further embodiment, water generated during the conversion is separated from the reactants. A caking of reactants on solid surfaces and the associated impairment of the reaction is hereby avoided. The operating errors and maintenance work associated with the caking in the reactor are also avoided. This applies in particular to the solid-state reaction in a mill or another mixed reactor.

The water can be separated in particular through evaporation of the amino acid chelates. Heat can hereby be supplied and/or the pressure can be reduced, under which the solid-state reaction is executed. The thermal activation can also take place through heat supply. Furthermore, the solid-state reaction can be executed in the presence of absorbent solids.

According to a further embodiment, the raw material is supplied dry to the process. The risk of caking on solid surfaces is hereby further avoided. The raw material preferably have a maximum water content of 5%. Furthermore, the maximum water content is preferably 2.5%.

According to a further embodiment, the activation and the conversion are performed in the same reactor. In a discontinuous reactor, the metal compounds can first be supplied and activated and then the amino acids can be added and the solid-state reaction can be executed. In a continuous straight-through reactor, the metal compounds can be supplied at a first supply position and, after flowing through an activation route at a second supply position, the amino acids can be supplied in order to flow through a reaction route jointly with the activated metal compounds.

According to another embodiment, the activation and the conversion are performed in different reactors. The different reactors can be discontinuous reactors, in which the mechanical activation and the conversion are executed separately and intermittently. Furthermore, the different reactors can be continuous reactors, in which the mechanical activation and the conversion are executed separately from each other in the pass-through.

According to a further embodiment, the activation and/or the conversion is executed in a vibrating grinding mill and/or in an agitator ball mill and/or in a drum mill and/or in another mixed reactor.

For the activation and optionally the solid-state reaction, the metal compounds and optionally the amino acids are preferably exposed to a mechanical stress through blows and pressure from a fine crushing machine. This is preferably an eccentric vibrating grinding mill.

In an eccentric vibrating grinding mill, the treated material is exposed to a mechanical stress in particular through blows and pressure. An eccentric vibrating grinding mill currently enables the most effective mechanical activation of metal compounds and is also very well suited for executing the solid-state reaction. The thermal activation can be effectuated simultaneously by the thermal energy released in the eccentric vibrating grinding mill.

A eccentric vibrating grinding mill suitable for use in the method according to the invention is described in DE 43 35 797 C2. Suitable vibrating grinding mills are sold by the company Siebtechnik, Mülheim an der Ruhr, Germany.

The activation and the conversion can be executed in the same mixed reactor, in different mixed reactors of the same type or in different types of mixed reactors. In particular, the activation can be executed in an eccentric vibrating grinding mill and the conversion in another type of mixed reactor.

According to one embodiment, the heat generated by operating the mixed reactor is used for the thermal activation and/or evaporation of the water. In particular, the heat generated by operating an eccentric vibrating grinding mill alone causes the thermal activation and/or evaporation of the water. For the heating-up of the mixed reactor, it is first heated up in a heating phase, if necessary. The heating phase can coincide with the mechanical activation.

According to one embodiment, the heat for the thermal activation and/or for the evaporation of water is supplied to the reactor. The thermal activation and/or the heat required for the evaporation can be supplied exclusively to the reactor from the outside. If necessary, heat in addition to the heat generated by the reactor can be supplied from the outside.

According to a further embodiment, the thermal activation and/or evaporation is executed at a temperature between 30° and 150° C. Furthermore, the thermal activation and/or the evaporation is executed at a temperature between 80° to 120° C.

According to a further embodiment, water created during the conversion is discharged from the reactor. The water can be discharged during the conversion once, intermittently or continuously.

According to a further embodiment, the conversion is continued during storage of the reaction product outside the reactor. The storage of the reaction product before use can be used for the continuation of the reaction. The availability of the reactor for the activation is hereby increased.

According to a preferred embodiment, the reaction product contains free reaction water for a continuation of the conversion during storage upon removal from the reactor. During storage at temperatures below the boiling point, in particular at room temperature, the free reaction water promotes a continuation of the reaction through ion transport. The reaction can thus be continued during storage. During the conversion in the reactor, the separation of the water from the reactants can be controlled such that a caking on solid surfaces is avoided and a sufficient share of free reaction water remains for a conversion during a subsequent storage in the reaction product.

According to a further embodiment, the free water content in the product is between 1% and 5%. The maximum water content in the product is preferably 3%. Furthermore, it is preferably approximately 2.5%. Product clotting and the impairment of the further processing are avoided with these water contents. The separation of the water during the conversion or respectively during a subsequent storage can be controlled such that the water content of the product is correspondingly reduced.

According to a further embodiment, the conversion takes place up to the complete stoichiometry. Double complexed copper glycinate consists of 29.7% by weight copper and 70.3% by weight glycine. The mass ratio of copper to glycine is thus 1:2.37. During the mechanical activation of CuO, an increased solubility depending on the glycinate reaction is achieved. The soluble copper content of copper glycinate can thereby be hyperstoichiometric and reach more than 35%.

According to a further embodiment, the amino acids are supplied to the conversion hyperstoichiometrically. A conversion is hereby promoted up to the full stoichiometry.

According to a further embodiment, the mass ratio of the metal oxides and/or the metal carbonates and/or the metal sulfates and/or metal chlorides and//or metal hydroxides to amino acids is 1:2 to 1:5.

According to one embodiment, amino acid chelate compounds of the copper and/or the zinc and/or the manganese and/or the iron and/or the magnesium and/or the calcium and/or the nickel and/or the cobalt are produced. According to a further embodiment, amino acid chelate compounds of the glycine and/or the lysine and/or the methionine and/or other amino acids and/or amino acid mixtures are produced.

For complex applications, e.g. as a fermentation additive and as a fertilizer additive, the method according to the invention permits the production of metal combination chelate compounds, in which mixtures of metal compounds e.g. of copper, zinc, iron and manganese are mechanically activated and brought to react e.g. with glycine through thermal activation The amino acid chelate compounds may have particles with a characteristic needle-shaped crystal structure. This structure is visible under a scanning electron microscope; FIG. 1 shows an example of an image from the scanning electron microscope (SEM).

The amino acid chelate compounds may contain neither sulfates nor chlorides and have a pH value in the range of 4-9. For use as animal food product additive, food product additive, dietary supplement and electroplating additive, this has the advantage that no undesired anions are incorporated.

The amino acid chelates may have an average particle size of 40 to 60 μm, preferably approximately 50 μm and up to 80% of the particles lie in the range of 0-100 μm, and are up to 2% larger than 500 μm. This grain size is particularly advantageous for use as animal food product additive, food product additive and dietary supplement, because a good distributability and mix quality are also provided at low concentrations.

The amino acid chelate compounds may have the advantage that they are producible with a relatively simple, stable and industrially suitable method.

The amino acid chelate compounds according to the invention may be used as animal food product additive and/or as fermentation additive and/or as fertilizer additive and/or as food product additive and/or as dietary supplement and/or as an electroplating additive.

The operability of the method according to the invention is represented for example by the CuO glycine system under stoichiometric conditions.

The dry synthesis can be described with the following mechanism:

1st Step
  Separate mechanical activation of CuO
2nd Step
  Addition of glycine.
  Thermal activation and temperature-defined conversion factor with mechanically activated CuO.

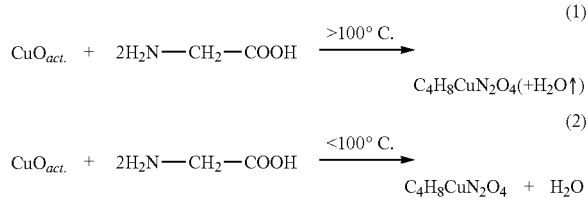

After this, in the first step, the separate mechanical activation of CuO in an eccentric vibrating grinding mill with e.g. an energy expenditure of approx. 300 kWh/t within a period of only approximately 30 to 60 min. The mill filling is 30%. Since approximately 90% of the applied energy is converted to heat in grinding processes, temperatures between 30 and 150° C. result for a non-thermostatic mill.

After the mechanical activation of CuO is complete, the mill filling is increased to 100% in the second step by the addition of glycine. With an energy expenditure of only approximately 5 kWh/t, CuO and glycine are brought to react in a few minutes. The speed of the reaction depends on the operating temperature of the mill, which causes the thermal activation. The degree of thermal activation is determined by the level of the operating temperature. This procedure applies in the case of batch mode in a mill.

However, it is also possible to separate the mechanical and the thermal activation by a series connection. In this case, the decoupled thermal activation would be able to be executed in a second thermostatic vibrating grinding mill or a thermostated conventional drum mill or respectively a thermostated agitator ball mill or in a thermostated mixer.

At temperatures greater than 100° C., the conversion lies e.g. between 95 and 100%. Below 100° C., the remaining reaction water enables the continuation of the reaction through storage up to full stoichiometric conversion.

Figure 2:
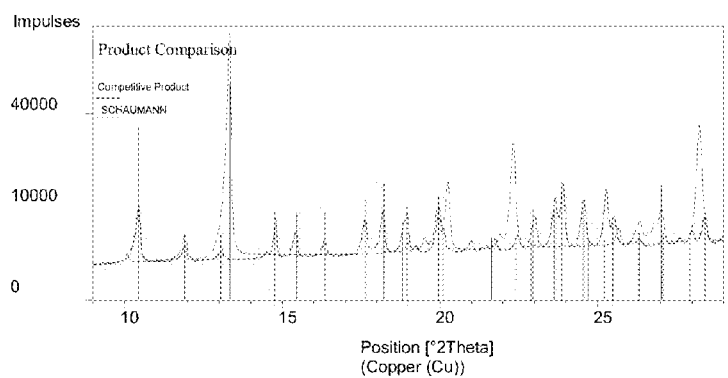
FIG. 2 shows an example of an X-ray diffraction diagram.

As control for the conversion rate, solubility tests with water are very reliable, wherein the blue colour of the tetramine complex becomes visible. In can be further proven through X-ray microstructure images that the formed compound is copperbis (glycinato) corresponding to glycine copper chelate according to the valid ASTM register. FIG. 2 shows an example of an X-ray diffraction diagram. The X-ray diffraction is based on the radiation of powder samples with monochromatic X-ray light; the reflected radiation intensity is measured depending on the diffraction angle. Intensity maxima thereby result for defined angles (2Θ), for which certain crystal surfaces, in this case crystal surfaces of the copper glycinate, reflect the X-rays. A clear assignment of crystalline substances is possible through comparison of the purest reference samples of the copper glycinate with defined diffraction patterns.

The object of the invention was extended to the dry synthesis of zinc chelate, manganese chelate, iron chelate, nickel chelate as well as magnesium chelate, calcium chelate and cobalt chelate and the reaction mechanism is confirmed in the same manner.

The method according to the invention is proven below based on examples.

EXAMPLE 1

The experiments for the method according to the invention were performed in a satellite grinding container with a volume of 2.7 l, which was flanged on an eccentric vibrating grinding mill of the type 656-0.5 ks. The grinding space of the satellite was lined with ceramic in order to avoid contamination.

The work was performed under the following operating conditions:
Speed: 960 min$^{-1}$
Amplitude: 12 mm
Grinding body: Steel 150 g of a copper oxide powder with a particle size of <100 µm were subjected to a mechanical activation for 15 minutes in the aforementioned satellites. At the beginning of the activation, the mill was 30° C. Then the mill was stopped and an additional 350 g of glycine were added to the activated copper oxide. The operating temperature of the mill was then 130° C. After a 10-minute thermal activation of the mixture, the process was ended and water vapour was released via a discharge valve. The slightly bluish colour of the product already indicated that a solid-state reaction must have taken place and that this was a new substance. The product was analysed for water solubility, crystal lattice structure, grain shape and grain size. The water solubility was 58% at room temperature after 10 min. and 98% after 60 min.; the dissolved Cu is thereby transferred to the known blue tetramine complex $[Cu(NH_3)_4]^{-2}$ in the presence of $NH_3$ ions. The examination of the crystalline structure with the X'Pert X-ray diffractometer from the Philips company showed at X-ray diffraction angle 2Θ 10.3 the main peak of bis (glycinato) copper ($C_4H_8CuN_2O_4$), which is listed in the ESTM register under the number 00-018-1714.

The result of the measurement of the X-ray diffractometer is shown in FIG. 2.

The grain shape was examined with the scanning electron microscope and produced the typical, needle-shaped crystals of the glycinates and their agglomerates. This is shown in FIG. 1. With respect to the bulk material properties, the particle distribution analysis found a $d_{50}$ value of 50 µm. The material is free-flowing, has a water content of <2% and is stable.

EXAMPLE 2

The application of the method according to the invention for the creation of copper, zinc, iron, manganese and nickel glycinates is demonstrated using a mixture of CuO, ZnO, $FeSO_4 \cdot H_2O$, $MnCO_3$ and NiO. For this, 150 g of the aforementioned mixture, in which each component made up 20%, were mechanically activated in the same test facility as in Example 1. The satellite was then opened and 300 g of glycine were added. At an operating temperature of 105° C., the thermal activation was connected for 5 min. The resulting water vapour was released via a discharge valve.

The solubility test with water at 25° C. produced full availability of all used metals after 60 min. The aqueous solution was clear and had a slightly olive mixture colour. X-ray structure images were not captured since the glycinate lines of the used metals overlap.

EXAMPLE 3

As a further example for the application of the method according to the invention, the production of alkaline earth glycinates, magnesium and calcium glycinate is described.

The same test facility as in Example 1 was used. The procedure for both syntheses was identical so that they are summarized here. 54 g of CaO or respectively MgO were each subjected to a 10-minute activation. In order to have a sufficiently high operating temperature for the thermal activation, the empty mill was already brought to an operating temperature of 110° C. before the experiments. After the mechanical activation, a thermal activation of respectively 15 min. took place in both cases. As solubility test, the water solubility was tested at respectively 45° C. over a time period of 10 min.

Upon addition of the generated calcium glycinate to water, a spontaneous complete solubility resulted and a pH value of 7.5 was reached in the crystal-clear solution.

The created magnesium glycinate led to a pH value of 8 upon addition to water, wherein a slightly cloudy solution resulted. The setting of pH 6 with HCl (component of gastric acid) gave a clear solution without the slightest traces of undissolved ingredients. Under the same solubility conditions, pure MgO in the presence of HCl is stable up to pH 0.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method for producing amino acid chelate compounds, wherein metal oxides and/or metal carbonates and/or metal sulfates and/or metal chlorides and/or metal hydroxides in solid form are activated mechanically and then the activated metal oxides and/or metal carbonates and/or metal hydroxides and/or metal sulfates and/or metal chlorides are brought together with amino acids in solid form and converted to amino acid chelate compounds in a solid-state reaction.

2. The method according to claim 1, in which at least one reactant is thermally activated.

3. The method according to claim 2, in which the thermal activation takes place at the same time as the mechanical activation and/or in which the thermal activation takes place at the same time as the conversion.

4. The method according to claim 1, in which water created during the conversion is separated from the reactants.

5. The method according to claim 4, in which the water is separated by evaporation from the reactants.

6. The method according to claim 1, in which the raw materials are added dry.

7. The method according to claim 1, in which the metal compounds are added as a mixture of loose particles and/or amino acids as a mixture of loose particles.

8. The method according to claim 1, in which the activation and the conversion are executed in the same reactor.

9. The method according to claim 1, in which the activation and the conversion are executed in different reactors.

10. The method according to claim 1, in which the activation and/or the conversion is executed in a vibrating grinding mill and/or in an agitator ball mill and/or in a drum mill and/or in another mixed reactor.

11. The method according to claim 1, in which the activation and/or the conversion takes place through mechanical stress through blows and pressure from a fine crushing machine.

12. The method according to claim 10, in which the vibrating grinding mill is an eccentric vibrating grinding mill.

13. The method according to claim 10, in which the heat generated through operation of the mixed reactor is used for the thermal activation and/or for the evaporation of the water.

14. The method according to claim 2, in which heat is supplied to the reactor for the thermal activation and/or for the evaporation of water.

15. The method according claim 2, in which the thermal activation and/or the evaporation is performed at a temperature between 30 and 150° C.

16. The method according to claim 15, in which the thermal activation and/or the evaporation is performed at a temperature of 80 to 120° C.

17. The method according to claim 1, in which water created during the conversion is removed from the reactor.

18. The method according to claim 1, in which the conversion is continued during storage of the reaction product outside the reactor.

19. The method according to claim 18, in which the reaction product contains free reaction water upon removal from the reactor.

20. The method according to claim 1, in which the content of free water in the product is between 1% and 3%.

21. The method according to claim 1, in which the conversion is performed up to the full stoichiometry.

22. The method according to claim 1, in which the amino acids are added to the conversion hyperstoichiometrically.

23. The method according to claim 1, in which the mass ratio of the metal oxides and/or the metal carbonates and/or the metal hydroxides and/or the metal sulfates and/or the metal chlorides to amino acids is 1:2 to 1:5.

24. The method according to claim 1, which is performed intermittently.

25. The method according to claim 1, which is performed continuously.

26. The method according to claim 1, in which amino acid chelates of the copper and/or the zinc and/or the manganese and/or the iron and/or the magnesium and/or the calcium and/or the nickel and/or the cobalt are produced.

27. The method according to claim 1, in which amino acid chelates of the glycine and/or the lysine and/or the methionine and/or other amino acids and/or amino acid mixtures are produced.

28. Amino acid chelate compounds prepared by the method of claim 1.

* * * * *